United States Patent [19]

Fung et al.

[11] Patent Number: 4,590,279

[45] Date of Patent: May 20, 1986

[54] PREPARATION OF (TRIFLUOROMETHYL)PYRIDINES UNDER LIQUID PHASE CONDITIONS

[75] Inventors: Alexander P. Fung, Pleasant Hill; Charles A. Wilson, Pittsburg, both of Calif.

[73] Assignee: The Dow Chemical Company, Midland, Mich.

[21] Appl. No.: 520,399

[22] Filed: Aug. 4, 1983

Related U.S. Application Data

[63] Continuation-in-part of Ser. No. 444,773, Nov. 26, 1982, abandoned.

[51] Int. Cl.$^4$ .......................................... C07D 213/26
[52] U.S. Cl. ..................................... 546/345; 546/346
[58] Field of Search ................ 546/345, 346; 570/160, 570/145

[56] References Cited

U.S. PATENT DOCUMENTS

| 2,347,846 | 5/1944 | Scherer | 260/384 |
|---|---|---|---|
| 2,436,357 | 2/1948 | Gochenour et al. | 570/160 |
| 2,442,290 | 5/1948 | Halbedel et al. | 260/464 |
| 2,516,402 | 7/1950 | McBee et al. | 260/290 |
| 3,711,486 | 1/1973 | Torba | 260/294.8 |
| 3,818,019 | 6/1974 | Rigterink | 424/263 X |
| 4,079,089 | 3/1978 | Klauke | 570/145 |
| 4,129,602 | 12/1978 | Sendlak | 570/145 |
| 4,184,041 | 1/1980 | Nishiyama et al. | 546/345 |
| 4,259,496 | 3/1981 | Whittaker | 546/345 |
| 4,266,064 | 5/1981 | Nishiyama et al. | 546/345 |
| 4,288,599 | 9/1981 | Nishiyama et al. | 546/345 |
| 4,429,132 | 1/1984 | Whittaker | 546/345 X |
| 4,448,967 | 5/1984 | Whittaker | 546/345 |

FOREIGN PATENT DOCUMENTS

| 0028870 | 5/1981 | European Pat. Off. . |  |
|---|---|---|---|
| 0063872 | 11/1982 | European Pat. Off. . |  |
| 7210371 | 3/1972 | Japan | 570/145 |
| 55-85564 | 6/1980 | Japan . |  |

OTHER PUBLICATIONS

Gerstenberger et al., Angew. Chem. Int. Ed. Engl. 20, (1981), pp. 647–667.
C.A. 94:47146h, (1981), Ishihara Sangyo Kaisha, Ltd.
Olah et al., J. Org. Chem., 44 (1979), pp. 3872–3881.

Primary Examiner—Joseph Paul Brust

[57] ABSTRACT (Trifluoromethyl)pyridine compounds are prepared by contacting (trichloromethyl)pyridine compounds with hydrogen fluoride in the presence of a catalytic amount of a catalyst selected from the group consisting of $FeCl_2$, $FeF_2$ and mixtures thereof under liquid phase conditions. The (trifluoromethyl)pyridine compounds are useful as intermediates for the preparation of agricultural chemicals.

21 Claims, No Drawings

PREPARATION OF (TRIFLUOROMETHYL)PYRIDINES UNDER LIQUID PHASE CONDITIONS

CROSS-REFERENCE TO RELATED APPLICATIONS

This is a continuation-in-part (CIP) of application Ser. No. 444,773, filed Nov. 26, 1982, now abandoned.

The present invention relates to a method of preparing (trifluoromethyl)pyridine compounds by reacting (trichloromethyl)pyridine compounds with hydrogen fluoride in the presence of a catalytic amount of a metal halide or metal halide/phosphorus halide catalyst under liquid phase conditions.

Fluorination of (trichloromethyl)pyridine compounds has been carried out by vapor phase fluorination which requires the use of high temperatures. Such vapor phase reactions suffer from disadvantages including, for example, energy costs associated with elevating the temperature of the reactants, the decomposition of starting materials and end products associated with high temperature vapor phase reaction systems and, furthermore, low conversion and/or low selectivities to the desired (trifluoromethyl)pyridine products. See, for example, Japanese Kokai Tokkyo Koho No. 80 85,564, June 27, 1980, Appl. No. 78/158,979, Dec. 22, 1978 and U.S. Pat. Nos. 4,266,064 and 4,288,599.

U.S. Pat. No. 4,184,041 discloses a method of preparing (trifluoromethyl)pyridine compounds by reacting a (trichloromethyl)pyridine compound with gaseous hydrogen fluoride at a temperature from 0°–50° C. While this method may produce small quantities of (trifluoromethyl)pyridine compounds, it is an unacceptable commerical means of producing (trifluoromethyl)pyridine compounds.

It is clearly evident that a more efficient method of preparing (trifluoromethyl)pyridine compounds is desirable in order to commercially produce such compounds.

It has been unexpectedly found that hydrogen fluoride and a metal halide or a metal halide/phosphorus halide catalyst, when combined with a (trichloromethyl)pyridine compound, produce (trifluoromethyl)pyridine compounds in a liquid phase halogen exchange reaction.

SUMMARY OF THE INVENTION

Briefly, in accordance with the present invention, a (trifluoromethyl)pyridine compound can be prepared in a liquid phase halogen (fluorine-chlorine) exchange reaction of an appropriate (trichloromethyl)pyridine compound. The (trichloromethyl)pyridine compound, containing one or two trichloromethyl groups, may optionally have substituents in other pyridine ring positions in addition to the trichloromethyl substituents.

The present method is conducted by contacting a (trichloromethyl)pyridine compound with hydrogen fluoride in the presence of a catalytic amount of a metal halide or a metal halide/phosphorus halide catalyst under liquid phase conditions sufficient to form the desired (trifluoromethyl)pyridine compound.

Of particular interest in the practice of the present invention is a method of preparing 2,3-dichloro-5-(trifluoromethyl)pyridine from 2,3-dichloro-5-(trichloromethyl)pyridine. Also of interest is the preparation of 2-chloro-5-(trifluoromethyl)pyridine from 2-chloro-5-(trichloromethyl)pyridine and the preparation of 2,6-dichloro-3-(trifluoromethyl)pyridine from 2,6-dichloro-3-(trichloromethyl)pyridine. These compounds are useful as intermediates in the manufacture of herbicides.

The present method provides a commerically efficient means of producing (trifluoromethyl)pyridine compounds in a liquid phase reaction system. The liquid phase condition provides a reaction where the desired (trifluoromethyl)pyridine compounds are produced in a selective manner. Additionally, the present liquid phase reaction may be run continuously by the addition of starting materials to a reaction vessel while the desired (trifluoromethyl)pyridine product, which generally has a boiling point less than the temperature at which the reaction is conducted, is collected by the condensation of (trifluoromethyl)pyridine vapors.

DETAILED DESCRIPTION OF THE EMBODIMENTS

In the practice of the present invention a (trichloromethyl)pyridine compound is contacted with hydrogen fluoride and a catalytic amount of a metal halide or a metal halide/phosphorus halide catalyst, hereinafter referred to as "catalyst", under liquid phase reaction conditions.

(Trichloromethyl)pyridine compounds employed as the starting material are unsubstituted or substituted-(trichloromethyl)pyridine compounds containing one or two trichloromethyl groups. The trichloromethyl groups may be in $\alpha$, $\beta$, or $\gamma$ ring positions. The pyridine ring optionally contains other substituents, besides the $CCl_3$ groups, which do not affect the halogen exchange reaction of this invention. Such substituents include, for example, Cl, Br, I, or F. Preferred (trichloromethyl)pyridine compounds include mono- or dichloro-$\beta$-trichloromethyl pyridine, such as, 2,3-dichloro-5-(trichloromethyl)pyridine; 2-chloro-5-(trichloromethyl)pyridine; and 2,6-dichloro-3-(trichloromethyl)pyridine.

The (trichloromethyl)pyridine compounds, described herein are known compounds and are prepared in any of a number of well known procedures. U.S. Pat. Nos. 3,787,420; 3,743,648; 4,331,811; 4,184,081 and 3,818,019, all of which are incorporated herein by reference, disclose methods of preparing (trichloromethyl)pyridines and halo(trichloromethyl)pyridines.

Hydrogen fluoride is employed as the source of fluorine in the present reaction. The hydrogen fluoride is introduced into the present reaction as hydrogen fluoride (anhydrous) or as hydrofluoric acid. The hydrogen fluoride is bubbled into the reaction as a gas or fed into the reaction as a liquid. Hydrogen fluoride (anhydrous) has a boiling point of 19.5° C. and the liquid and gas consist of associated molecules. Hydrogen fluoride (anhydrous) is a well-known compound and commercially available, generally in cylinders and tank cars. Hydrogen fluoride is also supplied as hydrofluoric acid which is hydrogen fluoride in aqueous solution. In the practice of the present invention, hydrogen fluoride is contacted with the other reactants and preferably hydrogen fluoride (anhydrous) is employed as the hydrogen fluoride source. Hydrogen fluoride is supplied at a ratio of at least about 3 moles per mole of mono-(trichloromethyl)pyridine compound and preferably an excess of this amount is employed. When bis-(trichloromethyl)pyridine compounds are employed as starting materials at least about 6 moles of HF per mole of bis-(trichloromethyl)pyridine compound are required to fluorinate the 2 trichloromethyl groups while it is preferred to supply an excess of this amount.

Metal halides are employed in catalytic amounts in the present reaction. Suitable metal halides include metal chlorides and metal fluorides. Suitable metal chlorides include $FeCl_2$, $FeCl_3$, $NbCl_5$, $TaCl_5$, $WCl_6$, $SnCl_4$, $TiCl_4$ or mixtures thereof. Suitable metal fluorides include $SbF_3$, $FeF_2$, $FeF_3$, $AgF$, $KF$, $CrF_2$ or mixtures thereof. The metal halide catalysts are added to the present reaction in catalytic amounts, generally from about 0.1 to about 20 mole percent based on the amount of (trichloromethyl)pyridine compound starting material present, and preferably from about 0.5 to about 10 mole percent. Preferred metal halide catalysts include $FeCl_3$ and $FeF_3$. Especially preferred metal halide catalysts are $FeCl_2$, $FeF_2$ and mixtures thereof.

Also, acceptable as a catalyst is a metal halide/phosphorus halide combination. Such a combination is achieved by supplying a phosphorus halide to the reaction mixture in addition to the metal halide catalyst. A preferred phosphorus halide is $PCl_5$.

Catalysts bonded to inert supports or precursor compounds which form the catalysts in situ are contemplated for use in the present invention. Examples of inert supports to which the catalysts may be bonded include graphite, alumina, silica, silica alumina, various clays and molecular sieves which are all well known in the art.

The present reaction is conducted under liquid phase conditions at a temperature usually under about 250° C., preferably at a temperature between about 100° C. and about 25° C. It is especially preferred to conduct the present reaction at a temperature between about 170° C. and about 180° C. The present halogen exchange reaction is typically conducted in the presence of agitation sufficient to maintain an essentially homogenous mixture of the reactants. The pressure at which the present reaction is carried out is not critical, but it is convenient to conduct the reaction at ambient atmospheric pressure.

In conducting the present reaction the order of addition of the reactants is not critical. Preferably, the (trichloromethyl)pyridine compound and the catalyst are admixed to form a reaction mixture and thereafter the hydrogen fluoride is added into this mixture, with stirring, until the reaction is completed, generally in from about 1 to about 100 hours. The exact time that the reaction is complete will vary on a variety of factors, such as, temperature, catalyst concentration, HF flow rate, degree of agitation and pressure. The hydrogen fluoride is fed into the reaction mixture as a liquid or, alternatively, may be bubbled or sparged into the reaction mixture as a gas.

In a preferred operation, 2,3-dichloro-5-(trichloromethyl)pyridine is mixed with a catalytic amount of $FeCl_3$ or $FeCl_2$ and then hydrogen fluoride (anhydrous) is continuously added into the reaction mixture while the temperature is increased to from about 150° C. to about 190° C. and preferably from about 170° C. to about 180° C. The reaction is usually completed in from about 1 to about 48 hours. The hydrogen fluoride (anhydrous) and HCl which escapes from the reaction mixture as vapor is conveniently collected employing conventional techniques such as by condensation.

A unique aspect of the present invention is presented when the desired (trifluoromethyl)pyridine compound which is being prepared has a boiling point below the temperature at which the reaction is conducted. When this occurs, the (trifluoromethyl)pyridine product vaporizes as it is formed and is conveniently collected in a pure form, separate from any (trichloromethyl)pyridine starting materials which generally have boiling points greater than the temperature at which the reaction is conducted. This allows the reaction to be run continuously by the substantially continuous addition or feeding of (trichloromethyl)pyridine compound and hydrogen fluoride to the reaction mixture.

The present halogen exchange reaction is characterized by the following chemical equation:

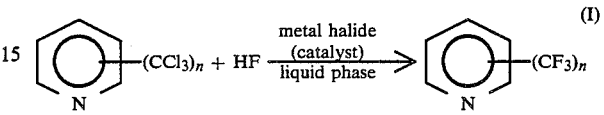

wherein n represents the integers 1 or 2. Preferred reactions are characterized as follows:

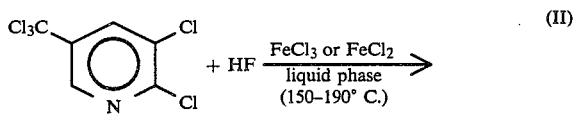

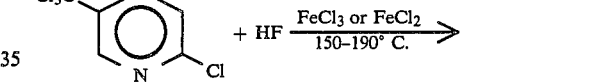

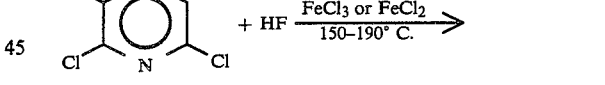

No attempt has been made to balance the above equations. In equation (I) above, the (trichloromethyl)pyridine compound may be further substituted as hereinbefore described and in equations (II), (III) and (IV), the $FeCl_3$ or $FeCl_2$ and 2,3-dichloro-5-(trichloromethyl)-pyridine, 2-chloro-5-(trichloromethyl)pyridine or 2,6-dichloro-3-(trichloromethyl)pyridine are mixed, to form a reaction mixture, and thereafter HF (anhydrous) is continuously added into this mixture as it is heated to a temperature between about 150° C. and about 190° C. This reaction is usually complete in from about 1 to about 48 hours.

The following examples are given to illustrate the invention and should not be construed as limiting its scope. No attempt has been made to balance any chemical equations described herein.

EXAMPLE 1

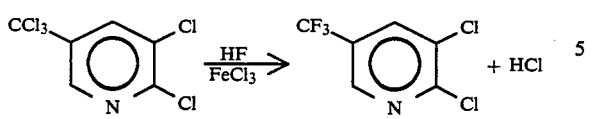

A 480 ml Teflon PFA ® reaction flask fitted with a PFA reflux condenser, an HF bleed tube, a magnetic stirrer and an optical pyrometer, was charged with 220 g of 2,3-dichloro-5-(trichloromethyl)pyridine and 9.5 g of FeCL$_3$. Anhydrous HF gas was introduced into the reaction mixture below the surface of the liquid as the mixture was heated to a temperature of 175° C. and maintained for a period of 14 hours. The anhydrous HF gas was bubbled into the reaction mixture throughout this 14 hour period. The reaction mixture was cooled and quenched with 100 g of ice water. The organic layer was separated, neutralized with NaHCO$_3$ and dried over Na$_2$SO$_4$. Analysis of the crude product employing standard gas-liquid chromatography (GLC) procedures indicated the product contained 58.1% 2,3-dichloro-5-(trifluoromethyl)pyridine, 24.4% 2,3-dichloro-5-(chlorodifluoromethyl)pyridine, 7.4% 2,3-dichloro-5-(dichlorofluoromethyl)pyridine and 10% 2-fluoro-3-chloro-5-(trifluoromethyl)pyridine. The crude product was then distilled resulting in 85 g of 2,3-dichloro5-(trifluoromethyl)pyridine which had a boiling point of 170°–172° C.

EXAMPLE 2

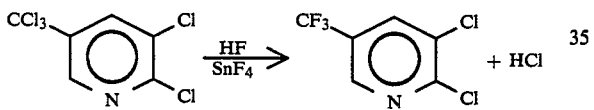

Into a 240 ml Teflon PFA ® reactor was charged 70 g of 2,3-dichloro-5-(trichloromethyl)pyridine and 2.33 g of tin tetrafluoride. Anhydrous HF gas was introduced into the reaction mixture below the surface of the liquid as the mixture was heated to a temperature of 170° C. over a period of 11 hours. The anhydrous HF was bubbled into the reaction period throughout this 11 hour period. Analysis of the crude product employing standard GLC procedures indicated the product contained 64% 2,3-dichloro-5-(trifluoromethyl)pyridine (includes isomers), 9.6% 2,3-dichloro-5-(chlorodifluoromethyl)pyridine, 2.2% 2,3-(dichlorofluoromethyl)pyridine and 24.2% 3-chloro-2-fluoro-5-(trifluoromethyl)pyridine.

EXAMPLE 3

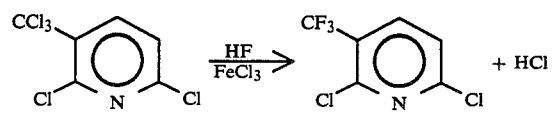

A 480 ml Teflon PFA ® reaction flask fitted with a PFA reflux condenser, an HF bleed tube, a magnetic stirrer and an optical pyrometer was charged with 220 g of 2,6-dichloro-5-(trichloromethyl)pryidine and 6.71 g (5 mole %) of FeCl$_3$. Anhydrous HF gas was introduced into the reaction mixture below the surface of the liquid as the mixture was heated to a temperature of 180° C. and maintained for a period of 19.5 hours. The reaction mixture was cooled and quenched with 150 g of ice water. The organic layer was separated, neutralized with NaHCO$_3$ and dried over MgSO$_4$. Analysis of the crude product employing standard GLC procedures indicated that the reaction was completed. The crude product was then distilled under reduced pressure (110° C./85 mm) resulting in 125 g of 2,6-dichloro-5-(trifluoromethyl)pyridine which corresponds to a yield of 70% of theoretical.

EXAMPLE 4

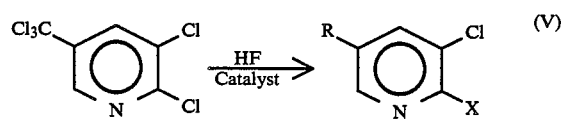

R=CF$_3$, CF$_2$Cl, CFCl$_2$ or CCl$_3$
X=Cl or F 2,3-Dichloro-5-(trichloromethyl)pyridine was reacted with HF (anhydrous) and various metal halide or metal halide/phosphorus halide catalysts under various temperature and time conditions. The products were analyzed employing standard GLC procedures to determine the area percent of the reaction products (area under the curve) and conversion of starting materials. The reaction products included compounds of Formula (V) above wherein R represents —CF$_3$ (the desired product), —CF$_2$Cl, —CFCl$_2$ or —CCl$_3$ (starting material) and X represents Cl or F. Also produced is the ring fluorinated compound which is represented by Formula (V) above when R represents CF$_3$ and X represents F. The results are indicated below in Table 1.

TABLE 1

| Run # | Catalysts | Amount of Catalysts (mole %) | Reaction Time (hrs) | Reaction Temperature (°C.) | X = Cl* R = CF$_3$ | X = Cl R = CF$_2$Cl | X = Cl R = CFCl$_2$ | X = Cl R = CCl$_3$ | X = F R = CF$_3$ |
|---|---|---|---|---|---|---|---|---|---|
| 1 | SbF$_3$/PCl$_5$ | 3.5/3.5 | 48 | ≦185 | 49 | 43 | 2 | 2 | 5 |
| 2 | TiCl$_4$/PCl$_5$ | 2/2 | 23 | ≦200 | 66 | 17 | 1 | 1 | 15 |
| 3 | AgF/PCl$_5$ | 2/2 | 45 | ≦180 | 51 | 37 | 8 | 1 | 2 |
| 4 | KF/PCl$_5$ | ≦100/100 | 49 | ≦185 | 3 | 12 | 71 | 11 | 3 |
| 5 | SnCl$_4$ | 4.5 | 14 | ≦180 | 43 | 15 | 2 | 1 | 39 |
| 6 | CrF$_2$ | 6.5 | 35 | 170 | 65 | 22 | 2 | 1 | 10 |
| 7 | WCl$_6$ | 1.7 | 34 | 175 | 50 | 37 | 8 | 1 | 4 |
| 8 | TaCl$_5$ | 1.2 | 22 | 165 | 59 | 32 | 5 | 0.5 | 3.5 |
| 9 | CoCl$_2$ | 4 | 22 | 175 | 1 | 12 | 67 | 20 | — |
| 10 | NbCl$_5$ | 1.6 | 15 | 175 | 43 | 25 | 12 | 1 | 19 |
| 11 | MnF$_3$ | 4 | 29 | 175 | 1 | 15 | 73 | 11 | — |
| 12 | SnCl$_4$ | — | — | 190 | o.h. 53 pot 47.5 | 34 43.5 | 5 5.7 | — — | 8 2 |
| 13 | SnF$_4$ | 4.5 | 11 | 170 | 66.5 | 10 | 2 | 1 | 20.5 |

TABLE 1-continued

| Run # | Catalysts | Amount of Catalysts (mole %) | Reaction Time (hrs) | Reaction Temperature (°C.) | X = Cl* R = CF$_3$ | X = Cl R = CF$_2$Cl | X = Cl R = CFCl$_2$ | X = Cl R = CCl$_3$ | X = F R = CF$_3$ |
|---|---|---|---|---|---|---|---|---|---|
| 14 | FeCl$_3$ | 5.2 | 18 | 170 | 48 | 47 | 1 | 0.1 | 4 |
| 15 | FeCl$_3$ | 5.2 | 16.5 | 190 | 46 | 42 | 1 | — | 11 |
| 16 | FeCl$_3$ | 0.5 | 15 | 170 | 13.3 | 60.6 | 17.6 | 2.3 | <1 |
| 17 | FeCl$_3$ | 10 | 15 | 170 | 70.1 | 8.3 | 3.4 | — | 18.2 |
| 18 | FeCl$_3$ | 7 | 14 | 175 | 60 | 24 | 4 | — | 8 |

*includes the isomer where X = F and R = CF$_2$Cl

EXAMPLE 5

Substantially the same procedure of Example 4 was carried out employing various catalysts under varying temperature and time conditions. The results are reported in Table 2.

TABLE 2

| Run # | Catalysts | Amount of Catalysts (mole %) | Reaction Time (hrs) | Reaction Temperature (°C.) | X = Cl R = CF$_3$ | X = F R = CF$_2$Cl | X = Cl R = CF$_2$Cl | X = Cl R = CFCl$_2$ | X = Cl R = CCl$_3$ | X = F R = CF$_3$ |
|---|---|---|---|---|---|---|---|---|---|---|
| 1 | — | — | 12 | 170 | — | — | Trace | 27 | 73 | — |
| 1a | — | — | 51.5 | ≦200 | — | 3 | 58 | 36 | 3 | — |
| 2 | FeCl$_3$ | 12.2 (7.5 w %) | 13 | 170 | 63 | 2 | 18 | <1 | — | 12 |
| 3 | FeCl$_3$ | 12.2 (7.5 w %) | 13 | 145 | 18 | 19 | 47 | 1 | — | 3 |
| 4 | FeF$_3$ | 7 | 12 | 170 | 45 | 8 | 38 | 3 | — | 9 |
| 5 | PCl$_5$ | 1.5 | 14.5 | 150 | — | 16 | 48 | 36 | — | — |
| 6 | FeCl$_3$/PCl$_5$ | 12.2/1.5 | 12.5 | 150 | 48 | 5 | 35 | 2 | — | 8 |
| 7 | FeCl$_3$/PCl$_4$ | 12.2/1.5 | 8 | 170 | 54 | 3 | 38 | — | — | 8 |
| 8 | TiCl$_4$ | 5.9 | 24 | 180 | 8 | 17 | 64 | 5 | — | — |
| 9 | AlCl$_3$ | 15 | 28 | 175 | <1 | 10 | 46 | 37 | — | — |
| 10 | ZrCl$_4$ | 7 | 22 | 175 | — | — | 8 | 56 | 47 | — |

EXAMPLE 6

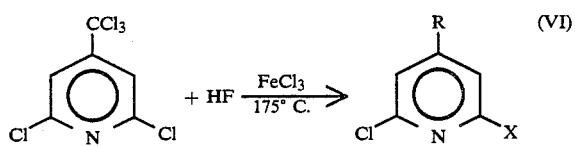

R represents CCl$_3$, CFCl$_2$, CF$_2$Cl or CF$_3$
X represents Cl or F.

A mixture containing 180 g of 2,6-dichloro-4-(trichloromethyl)pyridine and 12.2 g of FeCl$_3$ (11 mole %) was reacted with an excess molar amount of HF at 175° C. at atmospheric pressure for 7 hours employing substantially the same procedures as set forth in Examples 1–5. Analysis of reaction product indicated the formation of the following compounds as represented in Formula (VI) above (G.C. area %):

| R = CF$_3$ X = Cl | R = CF$_2$Cl X = F | R = CF$_2$Cl X = Cl | R = CFCl$_2$ X = Cl | R = CCl$_3$ X = Cl |
|---|---|---|---|---|
| 19.8% | 5.0% | 67.1% | 6.8% | None |

EXAMPLE 7

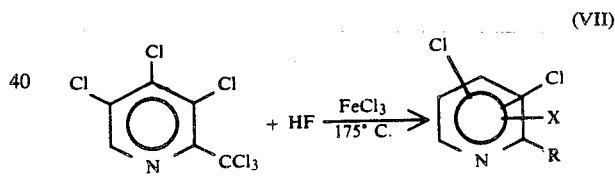

R=CF$_3$, CF$_2$Cl, CFCl$_2$, CCl$_3$
X=Cl or F

Substantially the same procedures of Example 6 were employed except 165 g of 3,4,5-trichloro-2-(trichloromethyl)pyridine and 9.82 g of FeCl$_3$ (11 mole %) was reacted with a molar excess of HF for 26 hours at 175° C. and atmospheric pressure. The product distribution in G.C. area % was as follows:

| R = CF$_3$ X = Cl | R = CF$_2$Cl X = Cl | R = CFCl$_2$ X = Cl | R = CF$_3$ X = F |
|---|---|---|---|
| 30.5% | 68.5% | 0.5% | 0.5% |

EXAMPLE 8

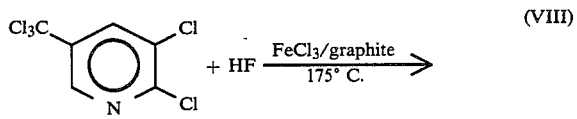

R=CCl$_3$, CCl$_2$F, CClF$_2$ or CF$_3$
X=Cl or F.

Substantially the same procedures of Examples 1–5 were employed except that 165 g. of 2,3-dichloro-5-(trichloromethyl)pyridine and 5.76 g of FeCl₃ (30–40%) in graphite (equivalent to 2 mole % FeCl₃) was reacted with an excess molar amount of HF at 175° C. at atmospheric pressure for 98 hours. Analysis of the reaction product indicated the formation of the following compounds as represented in Formula VIII above (G.C. area %) at the various times when samples were taken as listed in Table 3.

useful as a starting material in the preparation of 3-fluoro-5-(trifluoromethyl)-2-pyridinyloxy(or thio)-phenoxy propionic acid and derivatives thereof which are exceptional herbicides and are described in pending applications Ser. Nos. 389,840, filed June 18, 1982 and 401,057, filed July 23, 1982.

TABLE 3

$$Cl_3C\text{-pyridine-}Cl_2 + HF \xrightarrow{\text{FeCl}_3/\text{graphite}}_{175°\text{ C.}} R\text{-pyridine-}Cl,X$$

| | | Components in Area Percent | | | | | |
|---|---|---|---|---|---|---|---|
| | | R = CF₃ | R = CF₃ | R = CF₂Cl | R = CF₂Cl | R = CFCl₂ | R = CCl₃ |
| Sample | Time (hr) | X = F | X = Cl | X = F | X = Cl | X = Cl | X = Cl |
| 1 | 2 | nd* | nd | nd | 1.7 | 21.0 | 76.4 |
| 2 | 5 | nd | nd | nd | 6.7 | 57.8 | 35.5 |
| 3 | 17 | nd | 1.8 | 5.3 | 38.8 | 50.3 | 2.8 |
| 4 | 33 | 4.2 | 15.6 | 19.0 | 56.1 | 4.2 | 0.9 |
| 5 | 36 | 5.6 | 18.8 | 21.6 | 53.1 | 2.6 | 0.8 |
| 6 | 45 | 6.4 | 19.3 | 21.5 | 49.9 | 2.3 | 0.6 |
| 7 | 53 | 9.0 | 24.4 | 22.2 | 41.6 | 1.3 | 0.1 |
| 8 | 60 | 11.2 | 34.6 | 26.6 | 24.2 | 1.2 | nd |
| 9 | 74 | 13.0 | 40.1 | 21.1 | 22.9 | 1.2 | nd |
| 10 | 82 | 17.9 | 41.7 | 19.6 | 17.3 | 0.5 | nd |
| 11 | 87 | 20.4 | 49.6 | 18.2 | 11.4 | 0.3 | nd |
| 12 | 95 | 22.3 | 54.0 | 15.5 | 7.6 | 0.2 | nd |
| 13 | 98 | 23.6 | 50.7 | 14.4 | 6.6 | 0.2 | nd |

*"nd" means "not detected".

From the above Examples it is seen that underfluorinated materials, i.e., (chlorodifluoromethyl)pyridines and (dichlorofluoromethyl)pyridines, are present in the reaction product mixture. These underfluorinated materials are separated from the desired (trifluoromethyl)pyridine products, employing known separatory techniques, and recycled into the present fluorination reaction to form the desired (trifluoromethyl)pyridine products.

Over-fluorinated materials are also formed in the present reaction, i.e., fluoro-(trifluoromethyl)pyridines or ring fluorinated pyridine compounds. These over-fluorinated materials are also readily separated from the desired (trifluoromethyl)pyridine product. When the over-fluorinated compounds are ring fluorinated pyridine compounds wherein the fluoro attached to the pyridine ring has displaced a chloro, the ring-fluoro is displaced by a chloro by reacting the over-fluorinated product with HCl optionally at superatmospheric pressures. This reaction with HCl forms the desired chloro-(trifluoromethyl)pyridines from the over-fluorinated fluoro-(trifluoromethyl)pyridine by-products. The reaction with HCl also forms chloro-(chlorodifluoromethyl)pyridines from an isomeric fluoro-(chlorodifluoromethyl)pyridine by-product. It is very desirable to reduce the amount of isomeric, i.e., fluoro-(chlorodifluoromethyl)pyridine, product because of the difficulty in separating it from the desired chloro-(trifluoromethyl)pyridine product.

In another aspect of the present invention, 3-chloro-2-fluoro-5-(trifluoromethyl)pyridine is prepared from 2,3-dichloro-5-(trichloromethyl)pyridine employing the procedures described herein whereby the conditions are controlled to optimize the formation of the over-fluorinated product, i.e., 3-chloro-2-fluoro5-(trifluoromethyl)pyridine. This over-fluorinated product is

EXAMPLE 9

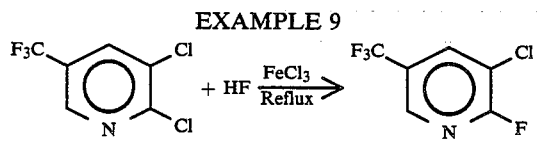

Substantially the same procedures of Example 6 were employed except that 143 g of 2,3-dichloro-5-(trifluoromethyl)pyridine (98% pure) and 4.37 g of FeCl₃ (5 mole %) was reacted with an excess molar amount of HF for 21 hours at 175° C. and atmospheric pressure. The product distribution in G.C. area % was as follows:

2,3-dichloro-5-(trifluoromethyl)pyridine . . . 67.7% (starting material)

3-chloro-2-fluoro-5-(trifluoromethyl)pyridine . . . 30.3%

EXAMPLE 10

2,3-Dichloro-5-(trifluoromethyl)pyridine

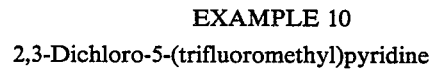

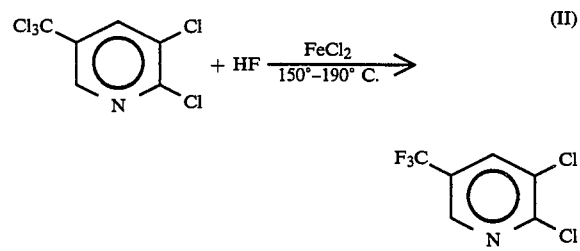

A 360 milliliter (ml) TEFLON ® PFA reaction flask, fitted with a PFA reflux condenser, an HF bleed tube, a magnetic stirrer and an optical pyrometer, was charged with 180 grams (g) of 2,3-dichloro-5-(trichloromethyl)pyridine and 4.3 g (5 mole percent) of FeCl₂. Anhydrous HF gas was introduced into the reaction mixture (~4 g/hr) below the surface of the liquid as the reaction mixture was heated to a temperature between 170° C. and 175° C. This temperature (170°–175° C.) was maintained for a period of 70 hours with constant agitation. Standard gas-liquid chromatography (GLC) analysis of the product indicated that the reaction product contained:

|  | Weight % |
|---|---|
| 2,3-dichloro-5-(trifluoromethyl)pyridine | 90.2% |
| 3-chloro-2-fluoro-5-(trifluoromethyl)pyridine | 6.1% |
| 2,3-dichloro-5-(chlorodifluoromethyl)pyridine | 3.6% |
| 3-chloro-2-fluoro-5-(chlorodifluoromethyl)-pyridine | <0.1% |

EXAMPLE 11

A Parr bomb, equipped with a condenser and a pressure release valve, was charged with 1,200 g of 2,3-dichloro-5-(trichloromethyl)pyridine and 28.6 g of FeCl$_2$ (5 mole %). Anhydrous HF gas was introduced into the reaction mixture (~3 g/hr) as the temperature was raised to 175° C. The pressure was maintained at 15 psig. After 95 hours, GLC analysis of the product (after the pressure was released and the product was allowed to cool to room temperature) indicated that the reaction product contained:

|  | Weight % |
|---|---|
| 2,3-dichloro-5-(trifluoromethyl)pyridine | 73.0% |
| 3-chloro-2-fluoro-5-(trifluoromethyl)pyridine | 1.7% |
| 3-chloro-2-fluoro-5-(chlorodifluoromethyl)-pyridine | 0.5% |
| 2,3-dichloro-5-(chlorodifluoromethyl)pyridine | 17.5% |
| 2,3-dichloro-5-(dichlorofluoromethyl)pyridine | 2.3% |

EXAMPLE 12

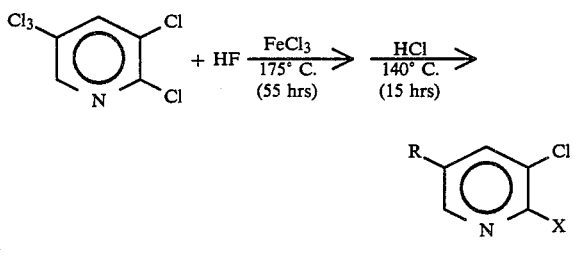

R=CCl$_3$, CCl$_2$F, CClF$_2$ or CF$_3$
X=Cl or F

Substantially the same procedures of Example 6 were repeated employing 180 g of 2,3-dichloro-5-(trichloromethyl)pyridine and 5 mole % (5.5 g) of FeCl$_3$. The reaction was run for 55 hours. After 55 hours, the temperature of the reactants was decreased to 140° C. and HCl was bubbled into the reaction mixture at a rate of 25 ml/minute for 15 hours. The product distribution in G.C. area was as follows:

| R = CF$_3$ X = Cl | R = CF$_3$ X = F | R = CF$_2$Cl X = F | R = CF$_2$Cl X = Cl | R = CFCl$_2$ or CCl$_3$ X = Cl |
|---|---|---|---|---|
| 79.4% | 1.8% | 0.1% | 14.2% | not detected |

On repeating the procedures described herein employing various catalysts and (trichloromethyl)pyridine starting materials, substantially the same results are obtained, i.e., preparation of (trifluoromethyl)pyridines is accomplished.

We claim:
1. A method of preparing a (trifluoromethyl)pyridine compound having the formula

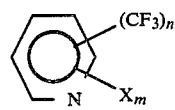

where X represents chlorine or fluorine, n is 1 or 2 and m is 0 or an integer of 1 to 4, which consists essentially of contacting a (trichloromethyl)pyridine compound having the formula

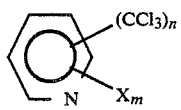

wherein X, m and n are as above-defined, with hydrogen fluoride in the presence of a catalytic amount of from about 0.1 to about 20 mole percent, based on the amount of (trichloromethyl)pyridine compound present, of a catalyst selected from the group consisting of FeCl$_3$, FeF$_3$, FeCl$_2$, FeF$_2$, NbCl$_5$, NbF$_5$, TaCl$_5$, TaF$_5$, WCl$_6$, WF$_6$, SnCl$_4$, SnF$_4$, TiCl$_4$, TiF$_4$, CrF$_2$, CrCl$_2$ and mixtures thereof in a liquid phase reaction at a temperature of from 100° C. to 250° C.

2. The method of claim 1 wherein said method is carried out at a temperature of from 130° C. to 190° C.

3. The method of claim 2 wherein said hydrogen fluoride is hydrogen fluoride (anhydrous).

4. The method of claim 1 wherein the pressure is at least one atmosphere.

5. The method of claim 4 wherein the hydrogen fluoride is employed in an amount of at least 3 moles per mole of pyridine compound.

6. The method of claim 5 wherein said catalyst is FeCl$_3$ and the FeCl$_3$ is present in the reaction mixture in an amount of from about 0.1 to about 20 mole percent based on the molar quantity of (trichloromethyl)pyridine present in the reaction mixture.

7. The method of claim 6 wherein said (trifluoromethyl)pyridine compound is 2,3-dichloro-5-(trifluoromethyl)pyridine and said (trichloromethyl)pyridine compound is 2,3-dichloro-5-(trichloromethyl)pyridine.

8. The method of claim 7 wherein said 2,3-dichloro-5-(trichloromethyl)pyridine is mixed with FeCl$_3$ to form a reaction mixture and then said hydrogen fluoride (anhydrous) is added to said reaction mixture for a time sufficient to form said 2,3-dichloro-5-(trifluoromethyl)pyridine.

9. The method of claim 8 wherein said temperature is from about 160° C. to about 180° C. and the FeCl$_3$ concentration is from about 0.5 to about 10 mole percent.

10. The method of claim 9 wherein said temperature is from about 170° C. to about 175° C.

11. The method of claim 6 wherein said (trifluoromethyl)pyridine compound is 3-chloro-2-fluoro-5-(trifluoromethyl)pyridine and said (trichloromethyl)pyridine compound is 2,3-dichloro-5-(trichloromethyl)pyridine.

12. The method of claim 6 wherein said (trifluoromethyl)pyridine compound is 2-chloro-5-(trifluoromethyl)pyridine and said (trichloromethyl)pyridine compound is 2-chloro-5-(trichloromethyl)pyridine.

13. The method of claim 5 wherein said catalyst is $FeF_3$ and the $FeF_3$ is present in the reaction mixture in an amount of from about 0.1 to about 20 mole percent based on the molar quantity of (trichloromethyl)pyridine present in the reaction mixture.

14. The method of claim 13 wherein said (trifluoromethyl)pyridine compound is 2,3-dichloro-5-(trifluoromethyl)pyridine and said (trichloromethyl)pyridine compound is 2,3-dichloro-5-(trichloromethyl)pyridine.

15. The method of claim 14 wherein said 2,3-dichloro-5-(trichloromethyl)pyridine is mixed with $FeF_3$ to form a reaction mixture and then said hydrogen fluoride (anhydrous) is added to said reaction mixture for a time sufficient to form said 2,3-dichloro-5-(trifluoromethyl)pyridine.

16. The method of claim 15 wherein said temperature is from about 160° C. to about 180° C. and the catalyst concentration is from about 0.5 to about 10 mole percent.

17. The method of claim 16 wherein said temperature is from about 170° C. to about 175° C.

18. The method of claim 13 wherein said (trifluoromethyl)pyridine compound is 3-chloro-2-fluoro-5-(trifluoromethyl)pyridine and said (trichloromethyl)pyridine compound is 2,3-dichloro-5-(trichloromethyl)pyridine.

19. The method of claim 13 wherein said (trifluoromethyl)pyridine compound is 2-chloro-5-(trifluoromethyl)pyridine and said (trichloromethyl)pyridine compound is 2-chloro-5-(trichloromethyl)pyridine.

20. The method of claim 1 wherein a chloro substituted-2-(trifluoromethyl)pyridine is prepared from a chloro substituted-2-(trichloromethyl)pyridine.

21. The method of claim 1 wherein a chloro substituted-4-(trifluoromethyl)pyridine is prepared from a chloro substituted-4-(trichloromethyl)pyridine.

* * * * *